United States Patent [19]

Riebel et al.

[11] 4,219,511
[45] Aug. 26, 1980

[54] PREPARATION OF O,O-DIETHYL-O-(1-PHENYL-2-CYANO-PROP-1-ENYL)-THIONOPHOSPHORIC ACID ESTER

[75] Inventors: Hans-Jochem Riebel, Selters; Claus Stölzer, Wuppertal, both of Fed. Rep. of Germany

[73] Assignee: Bayer Aktiengesellschaft, Leverkusen, Fed. Rep. of Germany

[21] Appl. No.: 29,815

[22] Filed: Apr. 13, 1979

[30] Foreign Application Priority Data

May 5, 1978 [DE] Fed. Rep. of Germany ....... 2819825

[51] Int. Cl.$^2$ .............................................. C07F 9/165
[52] U.S. Cl. ..................................... 260/973; 260/940
[58] Field of Search ................................ 260/973, 940

[56] References Cited

U.S. PATENT DOCUMENTS 3,775,517  11/1973  Riebel et al. ......................... 260/940

OTHER PUBLICATIONS

Conant et al., "The Chemistry of Organic Compounds", Third Edition, Macmillan Co., N.Y., (1947), pp. 93–94.

Primary Examiner—Anton H. Sutto
Attorney, Agent, or Firm—Sprung, Felfe, Horn, Lynch & Kramer

[57] ABSTRACT

In the preparation of O,O-diethyl-O-(1-phenyl-2-cyano-prop-1-enyl)-thionophosphoric acid ester by reacting a benzoic acid ester with propionitrile in the presence of an alkali metal alcoholate and then reacting the reaction mixture with O,O-diethyl-thionophosphoric acid diester chloride, the improvement which comprises employing about 5 to 50 moles of the propionitrile per mole of benzoic acid ester, distilling off the alcohol obtained during the reaction of propionitrile, benzoic acid ester and alcoholate before the addition of the O,O-diethyl-thionophosphoric acid diester chloride, and maintaining the volume of the reaction mixture approximately constant by adding propionitrile during the distillation. Advantageously the alcoholate is sodium methylate, ethylate or tert.-butylate or potassium methylate, ethylate or tert.-butylate, the reaction is effected at about 80° to 120° C., about 5 to 25 moles of propionitrile are employed per mole of benzoic acid ester, about 1 to 1.3 moles of benzoic acid ester and about 1 to 1.15 moles of alkali metal alcoholate are employed per mole of O,O-diethyl-thionophosphoric acid diester chloride, and the benzoic acid ester is the methyl ester or ethyl ester.

8 Claims, No Drawings

PREPARATION OF O,O-DIETHYL-O-(1-PHENYL-2-CYANO-PROP-1-ENYL)-THIONOPHOSPHORIC ACID ESTER

The invention relates to an unobvious process for the preparation of O,O-diethyl-O-(1-phenyl-2-cynao-prop-1-enyl)-thionophosphoric acid ester, which is a known compound suitable for combating arthropods.

It is already known that O,O-diethyl-O-(1-phenyl-2-cyano-prop-1-enyl)-thionophosphoric acid ester can be prepared by reacting O,O-diethyl-thionophosphoric acid diester chloride with 2-benzoyl-propionitrile in the presence of an acid acceptor and an inert diluent. The 2-benzoyl-propionitrile required as a starting material in that process can be prepared, for example, from benzoic acid ethyl ester and propionitrile in the presence of sodium methylate.

It is also known that O,O-diethyl-O-(1-phenyl-2-cyano-prop-1-enyl)-thionophosphoric acid ester can be prepared in a "one-pot process" by reacting benzoic acid ethyl ester with propionitrile in the presence of sodium methylate and then reacting the reaction mixture with O,O-diethyl-thionophosphoric acid diester chloride, without intermediate isolation of 2-benzoyl-propionitrile (see U.S. Pat. No. 3,775,517).

Maximum yields of only 30 to 40% of theory, relative to benzoic acid ethyl ester or O,O-diethyl-thionophosphoric acid diester chloride, are achieved in the two known processes.

The following disadvantages are the cause, to a greater or lesser extent, of the unsatisfactory yield: inadequate mixing during the reaction of benzoic acid ethyl ester with propionitrile and alcoholates, noncompletion and insufficient selectivity of the individual reactions and, associated therewith, the effort required to separate off by-products. By-products which may be mentioned are, in particular, thionophosphoric acid trialkyl esters.

The present invention now provides a process, especially a "one-pot" process, for the preparation of O,O-diethyl-O-(1-phenyl-2-cyano-prop-1-enyl)-thionophosphoric acid ester by reacting a benzoic acid ester with propionitrile in the presence of an alkali metal alcoholate at a temperature between 50° and 150° C. and then reacting the reaction mixture with O,O-diethyl-thionophosphoric acid diester chloride, wherein the propionitrile used as a starting substance is employed in a large excess, and in particular in an amount of from 5 to 50 moles per mole of benzoic acid ester, the alcohol obtained during the reaction of propionitrile, benzoic acid ester and alcoholate is distilled off from the reaction mixture before adding O,O-diethyl-thionophosphoric acid diester chloride, and the volume of the reaction mixture is kept approximately constant by continuous addition of propionitrile.

Yields of 70–80% of theory, with an active compound content of 95%, can be obtained in the present process.

It is surprising that the process according to the invention can proceed so smoothly and selectively under the reaction conditions indicated and can give O,O-diethyl-O-(1-phenyl-2-cyano-prop-1-enyl)-thionophosphoric acid ester, which was hitherto obtained only in unsatisfactory yields, in a good yield and high purity. This is particularly true with regard to the fact that propionitrile is also already employed in excess in the known process and such a drastic increase in yield by using an even larger excess of propionitrile could not be expected.

The process according to the invention has a number of advantages. By using a large excess of propionitrile, the reaction mixture always remains easily stirrable; this means that the mixture can also be mixed during the entire reaction period without using another diluent. In addition, by continuously distilling off the alcohol from the reaction mixture, the reaction is steered in the desired direction; the yield and purity of the product are greatly improved. The excess propionitrile used as a diluent in the first stage is also used as such in subsequent phosphorylation stage. In general, further solvents or diluents are thus not necessary. The propionitrile distilled off can be re-used for further batches, after separating off the alcohol.

The course of the reaction can be illustrated by the equation which follows:

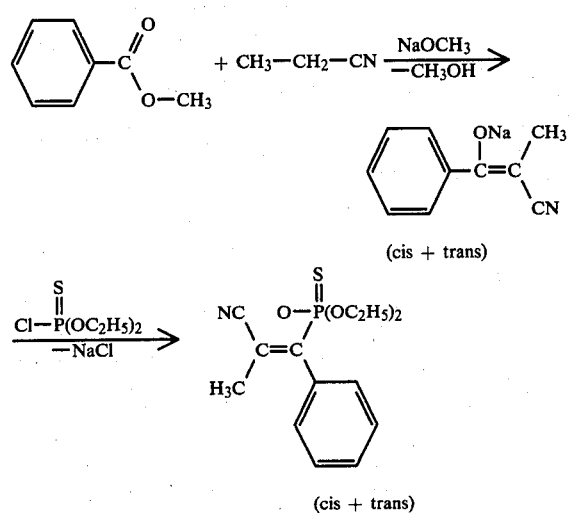

In addition to propionitrile and O,O-diethyl-thionophosphoric acid diester chloride, any desired alkyl esters of benzoic acid can also be employed as starting substances. Benzoic acid methyl ester and benzoic acid ethyl ester, especially benzoic acid methyl ester, are preferably used.

Alkali metal salts of any desired alcohols can be employed as auxiliary bases. Sodium methylate, ethylate or tert.-butylate or potassium methylate, ethylate or tert.-butylate, on particular sodium methylate, is preferably used.

The alcoholates can be employed in bulk or in the form of alcoholic solutions.

By using the starting material propionitrile in a large excess, it is possible, as mentioned, to dispense with the use of further diluents.

The reaction temperature can be varied within a substantial range. In general, the reaction is carried out at temperatures between about 50° and 150° C., preferably between about 80° and 120° C. In general, the reaction is carried out under normal pressure.

In carrying out the process according to the invention, in general about 1 to 3 moles, preferably about 1 to 1.3 moles, of benzoic acid ester, about 1 to 1.3 moles, preferably about 1 to 1.15 moles, of alcoholate and about 5 to 50 moles, preferably about 5 to 25 moles, of propionitrile are employed per mole of O,O-diethyl-thionophosphoric acid ester diester chloride.

The benzoic acid ester, alcoholates and propionitrile are appropriately mixed in the reaction flask at room temperature and the mixture is then heated to 80° to 120° C. for several hours, if appropriate while stirring. The alcohol formed during the reaction is then distilled off, the volume of the reaction mixture being kept constant by adding propionitrile. O,O-Diethyl-thionophosphoric acid diester chloride is then added slowly to the reaction mixture and the mixture is further kept at 80° to 120° C. for some time, while stirring. For working up, the propionitrile is first distilled off in vacuo. The residue is extracted by stirring with water or, if necessary, with dilute sodium hydroxide solution for the purpose of purification, and is taken up in toluene. After washing with water and drying, the toluene solution is evaporated in vacuo. The product is obtained as an oil and can be distilled. It can also be essentially freed from volatile constituents by "incipient distillation". that is to say, by prolonged heating to moderately elevated temperatures under reduced pressure, and can be purified in this manner. The NMR spectrum and the gas chromatogram serve as a criteria of purity.

The O,O-diethyl-O-(1-phenyl-2-cyano-prop-1-enyl)-thionophosphoric acid ester which can be prepared by the process according to the invention can, as already mentioned, be used for combating arthropods, especially insects and acarids.

The arthropod pests include: *Lepisma saccharina;* from the order of the Collembola, for example *Onychiurus aramtus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Phylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thruberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compound can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compound with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocynanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compound according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The process according to the invention is illustrated in more detail by the examples which follow:

EXAMPLE 1

A mixture of 156.5 g (1.15 mol) of benzoic acid methyl ester, 54 g (1 mol) of sodium methylate and 500 ml of propionitrile was stirred at a bath temperature of 120° C. (internal temperature 85° to 100° C.) for 3 hours. The methanol formed during the reaction was then distilled off under normal pressure. The volume of the reaction mixture was kept constant by simultaneously adding propionitrile dropwise. When about 200 ml of distillate had passed over, 188 g (1 mol) of O,O-diethyl-thionophosphoric acid diester chloride were allowed to run into the reaction mixture and the mixture was then stirred at a bath temperature of 120° C. for a further hour. Thereafter, the propionitrile was distilled off in vacuo and the residue was extracted by stirring with water (300 ml). The organic product phase was then taken up in 300 ml of toluene, the solution was washed once more with 250 ml of water and the organic phase was dried over calcium chloride. The toluene solution was concentrated and subjected to incipient distillation at 120° C./2 mm Hg. Yield: 220 g (71% of theory, relative to O,O-diethyl-thionophosphoric acid diester chloride).

Content according to the NMR spectrum and gas chromatogram: 95% of theory of O,O-diethyl-O-(1-phenyl-2-cyano-prop-1-enyl)-thionophosphoric acid ester with a refractive index of $n_D^{21}$ 1.5340.

EXAMPLE 2

A mixture of 156.5 g (1.15 mol) of benzoic acid methyl ester, 1 mol of technical grade sodium methylate solution and 500 ml of propionitrile was stirred at a bath temperature of 120° C. (internal temperature 85°–100° C.) for 3 hours. The methanol obtained during the reaction was then distilled off under normal pressure. The volume of the reaction mixture was kept constant by simultaneously adding propionitrile dropwise. When about 450 ml of distillate had passed over, 169.5 g (0.9 mol) of O,O-diethyl-thionophosphoric acid diester chloride were allowed to run into the reaction mixture and the mixture was then stirred at a bath temperature of 120° C. for a further hour. The propionitrile was then distilled off in vacuo and the residue was extracted by stirring with water (300 ml). After separating off the organic product phase, the oil thus obtained was taken up in 300 ml of toluene and the product phase was washed once again with 250 ml of water. The toluene solution was concentrated and subjected to incipient distillation up to 120° C./2 mm Hg.

Yield: 210 g (75% of theory, relative to O,O-diethyl-thionophosphoric acid diester chloride).

Content according to the NMR spectrum and gas chromatogram: 95% of theory of O,O-diethyl-O-(1-phenyl-2-cyano-prop-1-enyl)-thionophosphoric acid ester.

EXAMPLE 3

A mixture of 2.04 kg (15 mol) of benzoic acid methyl ester, 2.11 kg (10 mol) of technical grade sodium methylate solution and 5 liters of propionitrile was heated to the boil (bath temperature about 130° C.; internal temperature 85°–100° C.), while stirring, in a 20 liter flask which had a ground glass flange and was provided with a 40 cm long Vigreux column and a distillation bridge. While the methanol which was initially used as the solvent and was formed during the reaction was distilled off, the volume of the reaction mixture was kept approximately constant by continuously adding propionitrile (about 6.5 liters). When about 8.1 liters of distillate had passed over, 1.7 kg (9.01 mol) of O,O-diethyl-thionophosphoric acid diester chloride were allowed to run into the reaction mixture in the course of 15 minutes and, after the mixture had been stirred at a bath temperature of 120° C. for a further hour, the solvent was distilled off in vacuo. The residue was stirred with 3 liters of dilute sodium hydroxide solution and the product phase was extracted with 6 liters of toluene. The toluene solution was washed twice with 3 liters of water each time, dried over sodium sulphate, concentrated and subjected to incipient distillation up to 150° C./3 mm Hg.

Yield: 2.064 kg (73.6% of theory, relative to O,O-diethyl-thionophosphoric acid diester chloride).

Content according to the NMR spectrum and gas chromatogram: 95% of theory of O,O-diethyl-O-(1-phenyl-2-cyano-prop-1-enyl)-thionophosphoric acid ester.

It will be appreciated that the instant specification and examples are set forth by way of illustration and not limitation, and that various modifications and changes may be made without departing from the spririt and scope of the present invention.

What is claimed is:

1. In the preparation of O,O-diethyl-O-(1-phenyl-2-cyano-prop-1-enyl)-thionophosphoric acid ester by reacting a benzoic acid ester with propionitrile in the presence of an alkali metal alcoholate and then reacting the reaction mixture with O,O-diethyl-thionophosphoric acid diester chloride, the improvement which comprises employing about 5 to 50 moles of the propionitrile per mole of benzoic acid ester, distilling off the alcohol obtained during the reaction of propionitrile, benzoic acid ester and alcoholate before the addition of the O,O-diethyl-thionophosphoric acid diester chloride, and maintaining the volume of the reaction mixture approximately constant by adding propionitrile during the distillation.

2. A process according to claim 1, wherein the reaction is effected at about 50° to 150° C.

3. A process according to claim 1, wherein about 5 to 25 moles of propionitrile are employed per mole of benzoic acid ester.

4. A process according to claim 1, wherein about 1 to 3 moles of benzoic acid ester are employed per mole of the O,O-diethyl-thionophosphoric acid diester chloride.

5. A process according to claim 1, wherein about 1 to 1.3 moles of alkali metal alcoholate are employed per mole of O,O-diethyl-thionophosphoric acid diester chloride.

6. A process according to claim 1, wherein the benzoic acid ester is the methyl ester or ethyl ester.

7. A process according to claim 1, wherein the alcoholate is sodium methylate, ethylate or tert.-butylate or potassium methylate, ethylate or tert.-butylate.

8. A process according to claim 7, wherein the reaction is effected at about 80° to 120° C., about 5 to 25 moles of propionitrile are employed per mole of benzoic acid ester, about 1 to 1.3 moles of benzoic acid ester and about 1 to 1.15 moles of alkali metal alcoholate are employed per mole of O,O-diethyl-thionophosphoric acid diester chloride, and the benzoic acid ester is the methyl ester or ethyl ester.

* * * * *